United States Patent [19]

Kobayashi et al.

[11] Patent Number: 5,096,419
[45] Date of Patent: Mar. 17, 1992

[54] APPARATUS AND METHOD FOR DETECTING AN APICAL POSITION

[75] Inventors: Chihiro Kobayashi, Chiba; Kazunari Matoba, Kyoto, both of Japan

[73] Assignee: Kabushiki Kaisha Morita Seisakusho, Kyoto, Japan

[21] Appl. No.: 744,879

[22] Filed: Aug. 14, 1991

[51] Int. Cl.⁵ .............................................. A61C 19/04
[52] U.S. Cl. ...................................... 433/72; 128/776
[58] Field of Search ............................ 433/72, 75, 27; 128/774, 776, 777

[56] References Cited

U.S. PATENT DOCUMENTS

| | | | |
|---|---|---|---|
| 3,901,216 | 8/1975 | Felger | 433/27 |
| 4,353,693 | 10/1982 | Dery et al. | 433/27 |
| 4,447,206 | 5/1984 | Ushiyama | 433/27 |
| 4,526,179 | 7/1985 | Salesky | 433/72 |
| 5,017,134 | 5/1991 | Saito et al. | 433/72 |

Primary Examiner—Cary E. O'Connor
Attorney, Agent, or Firm—Koda and Androlia

[57] ABSTRACT

An apical position detection apparatus for detecting an apical position depending on the change in the impedance between a measuring electrode inserted in a root canal and an oral electrode connected to a soft oral tissue, the apparatus being characterized in that it comprises a signal output means which applies measurement signals with different frequencies between the measuring electrode and the oral electrode and a relative ratio detection means for calculating the ratio of root canal impedance values obtained depending on the measurement signals, whereby the detection apparatus detects the apical position by sensing that an equivalent impedance decreases and that the ratio of the root canal impedance values changes as the leading edge of the measuring electrode approaches the apical position. A method for detecting the apical position by using this apparatus is also disclosed.

3 Claims, 2 Drawing Sheets

APPARATUS AND METHOD FOR DETECTING AN APICAL POSITION

BACKGROUND OF THE INVENTION

1. Field of the Invention

The present invention relates to an improvement of an apparatus and a method for detecting an apical position applied to a root canal meter used for dental diagnosis and treatment.

2. Prior Art

Prior apparatuses used to measure root canal lengths by electrically detecting an apical position are classified into two types: a type for detecting the resistance between a measuring electrode inserted into a root canal and an oral electrode connected to an oral soft tissue (a gingiva, etc.) (refer to Japanese Patent Publication No. 62-25381 for example) and a type for detecting the impedance between the two electrodes (refer to Japanese Patent Publication No. 62-2817 for example).

The former type of the Japanese Patent Publication detects that the resistance decreases as the leading edge of the measuring electrode approaches the apical position. The latter detects that the impedance decreases as the leading edge of the measuring electrode approaches the apical position. Since the circuit between the measuring electrode and the oral electrode is assumed to be equivalent to a circuit comprising a resistor and a capacitor connected in parallel, the measurement principle of the latter type is suited for actual application. In particular, the latter type applies two signals with different frequencies between the two electrodes and detects the impedance of each signal, instead of simply detecting the impedance of the circuit, then sequentially compares the detection results to detect whether the leading edge of the measuring electrode has arrived at the apical position depending on the change in the difference between the impedance values.

The above-mentioned former type simply detects the resistance value between the two electrodes on the assumption that the inside of the root canal is dry. Therefore, if the inside of the root canal is wet, errors may occur. In actual practice, it is difficult to make measurements while the inside of the root canal is always dry. In actual clinical conditions, medical liquids and blood are present frequently in the root canal. Since the equivalent resistance in the root canal is decreased by the effect of such medical liquids, an apical position arrival mis-indication may appear even when the leading edge of the measuring electrode does not arrive actually at the apical position, or measurements may become impossible frequently. In addition, the resistance value is also affected by external factors such as the diameter of the apical foramen and the size of the measuring electrode like a file or reamer. Therefore, it is difficult to determine whether the change in the resistance value is caused by the change in the position of the file or reamer in the root canal or by other external factors, thus being apt to cause problems of improper indications.

The latter type have solved most of the above-mentioned problems. However, the type needs calibration at each measurement to eliminate the effects of the conditions in the root canal. In particular, when measuring a molar tooth with a plurality of root canals, calibration is necessary for each root canal, making operation troublesome and hindering treatment efficiency.

FIG. 4 is a graph illustrating this calibration. The abscissa of the graph indicates the position of the leading edge of the measuring electrode and the ordinate of the graph indicates the detection voltage corresponding to the impedance. The graph indicates detection values at two different frequencies $f_1$ and $f_2$ ($f_1 < f_2$). The detection values at the higher frequency are generally larger than those at the lower frequency. Near the apical position, the rate of increase in the detection values at the higher frequency is also higher than the rate of increase in the detection values at the lower frequency. These values change up and down depending on the conditions inside the root canal.

If it is assumed that the detection values at the dental neck section are $V_{10}$ and $V_{20}$, that the detection values at the apical positions are $V_1$ and $V_2$, and that the changes in the detection values due to the change in the position of the electrode are $\Delta V_1$ and $\Delta V_2$, the difference between the changes ($\Delta V_2 - \Delta V_1$) is not affected by the conditions inside the root canal, thus indicating a relative change in impedance depending on the frequency. This means that the following formula is established.

$$\Delta V_2 - \Delta V_1 = (V_2 - V_{20}) - (V_1 - V_{10}) = (V_2 - V_1) - (V_{20} - V_{10})$$

It is therefore necessary to conduct calibration to compensate for a bias corresponding to the second term, ($V_{20} - V_{10}$), of the above formula at each measurement by using the detection values at the dental neck section and to eliminate the effects of the conditions inside the root canal. This calibration is conducted by adjusting the offset of the detection apparatus of the latter type, for example by operating an adjustment resistor.

SUMMARY OF THE INVENTION

The inventors of the present invention gave attention to the above-mentioned matter. It is therefore an object of the present invention is to provide an apparatus and a method capable of accurately detecting the apical position without requiring troublesome calibration.

To achieve the above-mentioned object, the present invention provides an apical position detection apparatus being characterized in that it comprises a signal output means which applies measurement signals with different frequencies between a measuring electrode and an oral electrode and a relative ratio detection means for calculating the ratio of root canal impedance values obtained depending on the measurement signals, whereby the detection apparatus detects the apical position by sensing that an equivalent impedance decreases and that the ratio of the root canal impedance values changes as the leading edge of the measuring electrode approaches the apical position. The present invention also provides a detection method using the detection apparatus.

BRIEF DESCRIPTION OF THE DRAWINGS

The present invention is detailed below referring to the accompanying drawings.

FIG. 1 (b) shows a circuit equivalent to that shown in FIG. 1 (a);

DETAILED DESCRIPTION OF THE INVENTION

Figure 1A:
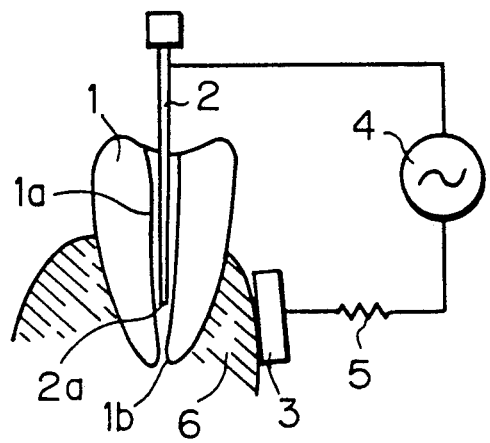
FIG. 1 (a) shows a measurement circuit used to explain the principle of the present invention.
Figure 1B:
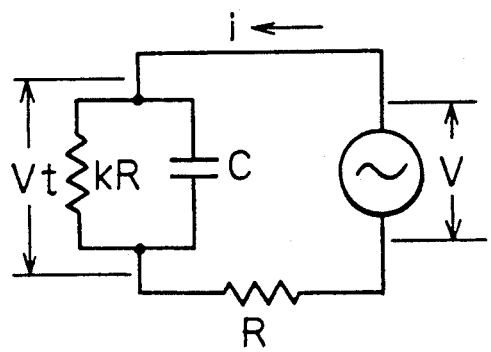

The function and principle of the present invention is explained below referring to FIG. 1. FIG. 1 (a) shows a measurement circuit and FIG. 1 (b) shows a circuit equivalent to the measurement circuit.

Referring to these figures, numeral 1 represents a tooth. Numerals 1a and 1b represent a root canal and an apical section respectively. Numeral 2 represents a measuring electrode. Numeral 2a represents the leading edge of the measuring electrode. Numeral 3 represents an oral electrode connected to a gingiva 6. Numeral 4 represents a measurement voltage generation circuit and numeral 5 represents a load current detection resistor. The circuit in the root canal, i.e., the circuit between the measuring electrode 2 and the oral electrode 3, can be assumed to be equivalent to a circuit comprising a resistor and a capacitor being connected in parallel. V represents measurement voltage, R represents the resistance value of the detection resistor 5. C represents the capacitance of the equivalent capacitor and kR represents the resistance of the equivalent resistor, where k is a coefficient. The equivalent circuit has the features described below:

(a) At the dental neck section, value C is very small and coefficient k is far larger than that obtained at the apical section. Therefore, value kR is large.

(b) At a measurement position closer to the apical section, value C increases exponentially and value kR decreases.

(c) At the apical section, approximate values of C and kR are 50 nF and 6.5 kΩ respectively. Hereafter, value C obtained at this time is referred to as Co.

(d) Coefficient k is determined depending on the environmental conditions inside the root canal, such as the presence of medical liquids and blood. If the root canal is filled with an electrically conductive liquid, value k becomes small. If the root canal is dry, value k becomes large. This change causes errors. Furthermore, value k also changes depending on the measurement position inside the root canal.

If it is assumed that the voltage to be applied to the equivalent circuit is Vt and the load current is i, the following formula is obtained.

$$i = Vt \cdot \left( \frac{1}{kR} + \omega C_0 \right)$$

where $\omega = 2\pi f$ and f is a frequency value.

$$\begin{aligned} V &= i \cdot R + Vt \\ &= Vt + Vt \cdot \left( \frac{1}{kR} + \omega C_0 \right) \times R \\ &= Vt \cdot \left( 1 + \frac{1}{k} + \omega C_0 R \right) \end{aligned}$$

$$\therefore Vt = \frac{V}{\left( 1 + \frac{1}{k} + \omega C_0 R \right)} \quad (1)$$

Figure 2:
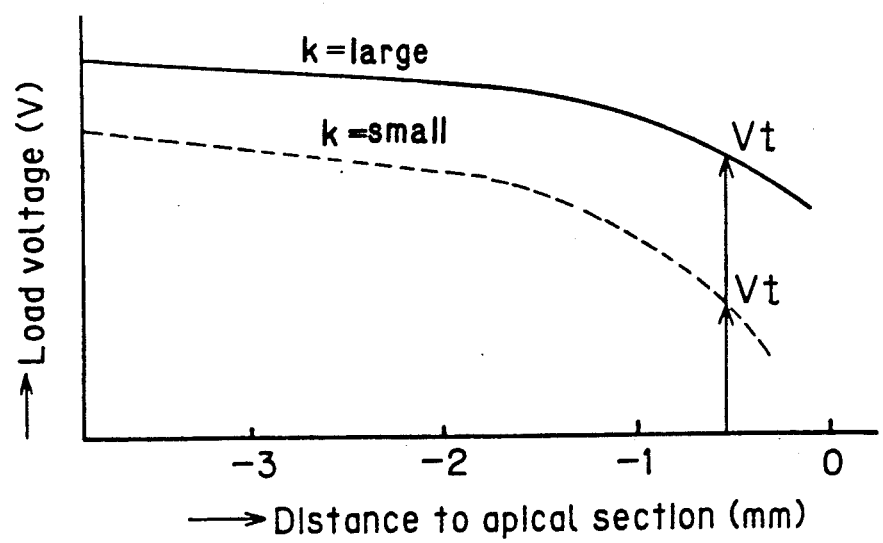
FIG. 2 is a graph illustrating the relationship between the load voltage (detection result) of the circuit and the distance to the apical section.

Since formula (1) includes 1/k in its denominator, value Vt changes depending on the environmental conditions inside the root canal and cannot be used as a detection value. FIG. 2 is a graph illustrating the relationship between the voltage and the measurement position inside the root canal. The abscissa of the graph indicates the distance from the leading edge 2a of the measuring electrode 2 to the apical section 1b and the ordinate of the graph indicates voltage Vt. The solid line represents the change in voltage Vt when value k is large and the broken line represents the change in voltage Vt when value k is small. At a measurement position close to the apical section, a great difference is found between the solid and broken lines. This indicates that the voltage values obtained at a measurement position close to the apical section cannot be used as detection values.

Described next is the method for detecting the difference between the impedance values corresponding to the signals with two different frequencies used in the latter type of the above-mentioned patent publication. With this method, two Vt values are obtained by using the above-mentioned formula (1) at two different frequencies and the difference between the two Vt values is calculated. More particularly, when angular frequencies $\omega$ and $5\omega$ are used for example:

$$\text{Difference} = \frac{V}{\left( 1 + \frac{1}{k} + \omega C_0 R \right)} - \frac{V}{\left( 1 + \frac{1}{k} + 5\omega C_0 R \right)} \quad (2)$$

$$= \frac{4\omega C_0 R V}{\left( 1 + \frac{1}{k} + \omega C_0 R \right)\left( 1 + \frac{1}{k} + 5\omega C_0 R \right)} \quad (3)$$

Formula (3) is thus obtained as shown above. According to this formula, calibration is necessary at each root canal measurement to cancel the effect of 1/k, except that $1/k << \omega CoR$.

On the other hand, the present invention obtains the ratio of the impedance values at two different frequencies to reduce the effect of coefficient k by using formula (4) described below.

$$\text{The ratio} = \frac{1 + \frac{1}{k} + \omega C_0 R}{1 + \frac{1}{k} + 5\omega C_0 R}$$

$$= \frac{1 + \frac{\omega C_0 R}{1 + \frac{1}{k}}}{1 + \frac{5\omega C_0 R}{1 + \frac{1}{k}}} \quad (4)$$

where k = 1 to 10.

With this formula, the effect due to the change in 1/k is made small by the division process used for obtaining the ratio. Therefore, this indicates that calibration is not necessary at each root canal measurement.

For example, C=100 nF, R=10 kΩ, f=1 kHz and k=1 to 10 are substituted in formula (4), the ratio values listed in the following table are obtained. As shown in the table, the ratio values are scarcely affected by the change in value k. This means that the effect due to the environmental conditions inside the root canal is canceled automatically by taking the ratio of the impedance values at two different frequencies. As a result, this method eliminates the need for calibration at each root canal measurement which is necessary in the type of the method which uses the difference between the impedance values. In addition, this method allows accurate measurement regardless of the environmental conditions inside the root canal.

higher stability and allows accurate measurement continuously regardless of moderately secular changes of circuit parts.

As understood according to the above descriptions, the present invention discloses an apical position detection method being characterized in that it comprises applying measurement signals with different frequencies between the measuring electrode and the oral electrode, calculating the ratios of the root canal impedance values obtained depending on the measurement signals and detecting the apical position by sensing the change in the ratio.

Obtaining the ratio of the detection values in this way automatically cancels the effects of external factors,

| k | 1 | 2 | 3 | 4 | 5 | 6 | 7 | 8 | 9 | 10 |
|---|---|---|---|---|---|---|---|---|---|---|
| Ratio | 0.25 | 0.24 | 0.23 | 0.23 | 0.23 | 0.23 | 0.23 | 0.23 | 0.23 | 0.23 |

EXAMPLE

Figure 3:
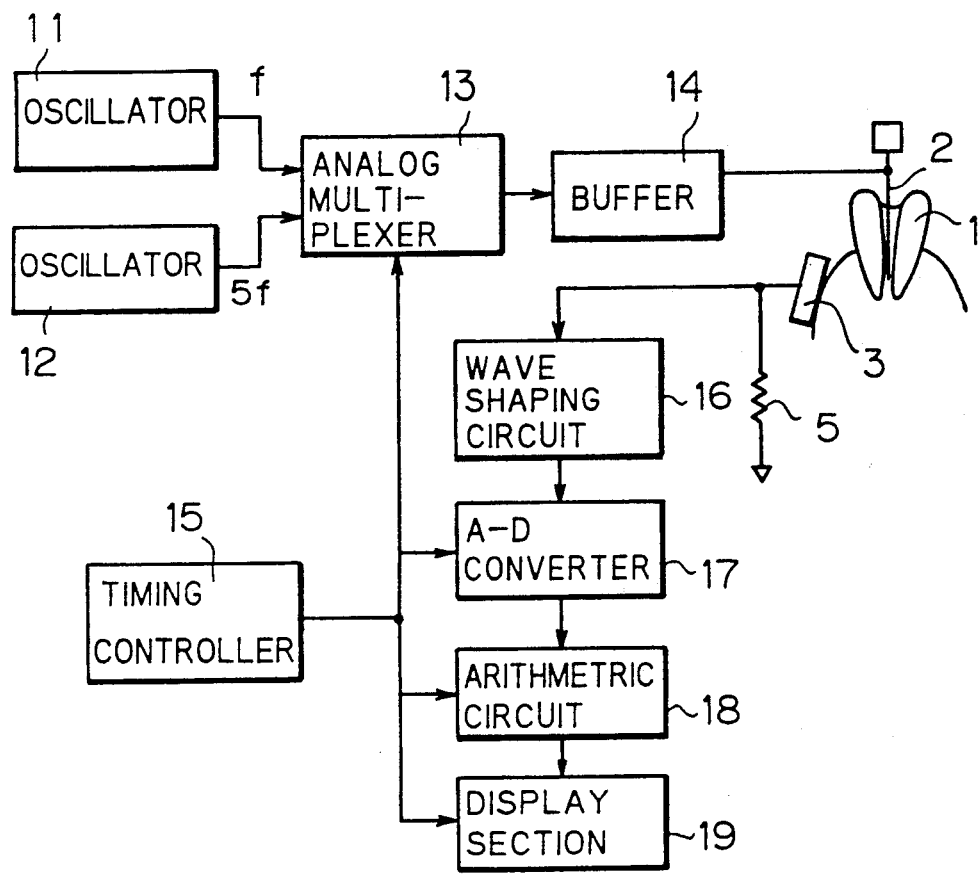
FIG. 3 is a block diagram of an example of the present invention.
Figure 4:
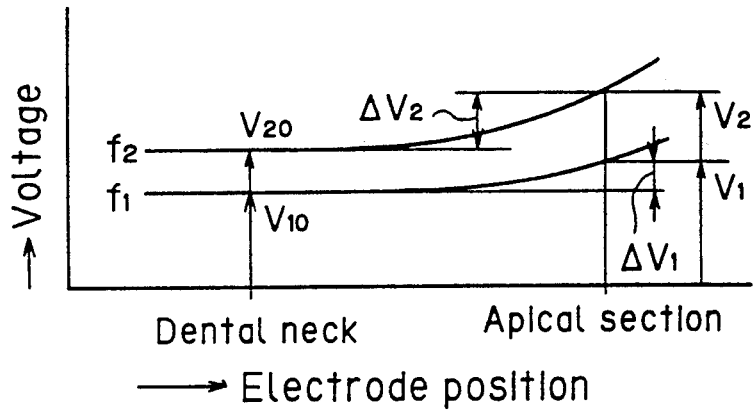
FIG. 4 is a graph used to explain the calibration of a conventional apparatus.

Next, an example of the present invention is explained below. Referring to the block diagram shown in FIG. 3, numeral 11 represents an oscillator generating a measurement signal with frequency f and numeral 12 represents an oscillator generating a measurement signal with frequency 5f. Numeral 13 represents an analog multiplexer, numeral 14 represents a buffer, numeral 15 represents a timing controller, numeral 16 represents a wave shaping circuit, numeral 17 represents an A-D converter, numeral 18 represents an arithmetic circuit and numeral 19 represents a display section. The block's measurement principle for measuring the apical section 1b is the same as that of the circuit shown in FIG. 1.

The timing controller 15 controls the operation timing of all circuits. By this control, the analog multiplexer 13 switches the outputs of the oscillators 11 and 12 every 100 msec for example. The output of the analog multiplexer 13 is applied to the measuring electrode 2 via the buffer 14. The load current is detected by the resistor 5 as a voltage value. The waveform of the voltage is shaped by the wave shaping circuit 16 and converted into digital data by the A-D converter 17. While latching the data, the arithmetic circuit 18 sequentially calculates the ratio between the data obtained by using the measurement signal with frequency f and the data obtained by using the measurement signal with frequency 5f. The result of the arithmetic operation is fed to the display section 19. The display section 19 can be made up of an appropriate device, such as a meter with a pointer, a signal sound generator, an intermittent sound generator or an intermittent light generator.

By the above-mentioned structure and operations, the result of the arithmetic operation is indicated by the display section 19. The detection value obtained at frequency 5f is generally higher than that obtained at frequency f. The rate of increase is larger at a position closer to the apical section. Since the ratio becomes larger as the leading edge 2a is moved closer to the apical section, the arrival of the leading edge 2a of the electrode 2 is displayed by the deflection of a pointer for example.

In the case of this example, the circuits subsequent to the multiplexer 13 are made up of a single system. Therefore, even if a part in the system is deteriorated and malfunctions, the effect of the malfunction is canceled by the division process used for obtaining the ratio. The apparatus is thus advantageous since it has such as the conditions inside the root canal, more particularly the difference caused by whether the root canal is dry or wet, and the difference caused by whether an electrically conductive liquid (medical liquid or blood) is present or not, as well as the diameter of the apical foramen and the size of the measuring electrode. This eliminates the need for troublesome calibration at each measurement. Furthermore, the effect due to deteriorated parts can be eliminated automatically. Moreover, the apparatus can reduce the adverse effect from hum noise or other noise from alternate current power supply. This apparatus can thus be incorporated in a scaler, making it easily applicable to the enlargement of the root canal. Therefore, the apparatus of the present invention is free from those problems encountered in the resistor detection type and the impedance detection type described in the above-mentioned patent publications. The apparatus can be operated easily and can ensure high measurement accuracy, applicable to a root canal meter which is easy to use clinically.

We claim:

1. An apical position detection apparatus for detecting an apical position depending on the change in the impedance between a measuring electrode inserted in a root canal and an oral electrode connected to a soft oral tissue, said apparatus being characterized in that it comprises:

a signal output means which applies measurement signals with different frequencies between said measuring electrode and said oral electrode; and a relative ratio detection means for calculating the ratio of root canal impedance values obtained depending on the measurement signals, whereby said detection apparatus detects the apical position by sensing that an equivalent impedance decreases and that the ratio of said root canal impedance values changes as the leading edge of said measuring electrode approaches the apical position.

2. An apical position detection method adapted such that an apical position is detected depending on the change in the impedance between a measuring electrode inserted in a root canal and an oral electrode connected to a soft oral tissue, said method being characterized in that it comprises:

applying measurement signals with different frequencies between said measuring electrode and said oral electrode;

calculating the ratio of root canal impedance values obtained depending on the measurement signals; and whereby the apical position is detected by sensing that an equivalent impedance decreases and that the ratio of said root canal impedance values changes as the leading edge of said measuring electrode approaches the apical position.

3. An apical position detection method according to claim 2 wherein the ratio of said impedance values are calculated by using formula (4) described below:

The ratio of said impedance values $$= \frac{1 + \dfrac{\omega C_0 R}{1 + \dfrac{1}{k}}}{1 + \dfrac{5\omega C_0 R}{1 + \dfrac{1}{k}}} \quad (4)$$

where k = 1 to 10 (a coefficient determined depending on the environmental conditions inside the root canal), $\omega = 2\pi f$ f = a frequency R = the resistance value of the detection resistor Co = the equivalent capacitance measured near the apical position.

* * * * *